(12) United States Patent
Yeh

(10) Patent No.: US 6,858,029 B2
(45) Date of Patent: Feb. 22, 2005

(54) SYSTEM FOR FIXING AND RECUPERATING VERTEBRAE UNDER TREATMENT

(76) Inventor: Chung-Chun Yeh, 16, Alley 1, Lane 65, Jen-Ai Road, Section 2, Taipei (TW)

( * ) Notice: Subject to any disclaimer, the term of this patent is extended or adjusted under 35 U.S.C. 154(b) by 2 days.

(21) Appl. No.: 10/134,529

(22) Filed: Apr. 30, 2002

(65) Prior Publication Data

US 2002/0169451 A1 Nov. 14, 2002

(30) Foreign Application Priority Data

May 2, 2001 (TW) .................................. 90207095 U

(51) Int. Cl.⁷ .................................................. A61B 17/58
(52) U.S. Cl. .................................................... 606/61
(58) Field of Search ........................ 606/54, 57, 58, 606/60, 61, 72, 73, 74, 105; 623/17.11, 17.16; 269/143, 249; 403/374.1, 374.2, 374.3, 374.4, 409.1

(56) References Cited

U.S. PATENT DOCUMENTS

| | | | | |
|---|---|---|---|---|
| 4,257,409 A | * | 3/1981 | Bacal et al. ................... 606/61 |
| 4,269,178 A | * | 5/1981 | Keene .......................... 606/61 |
| 4,422,451 A | * | 12/1983 | Kalamchi ..................... 606/61 |
| 4,611,582 A | * | 9/1986 | Duff ............................. 606/61 |
| 4,641,636 A | * | 2/1987 | Cotrel ........................... 606/61 |
| 5,352,225 A | * | 10/1994 | Yuan et al. .................... 606/61 |
| 5,391,168 A | * | 2/1995 | Sanders et al. ................ 606/61 |
| 5,401,269 A | * | 3/1995 | Buttner-Janz et al. ... 623/17.15 |
| 5,620,443 A | * | 4/1997 | Gertzbein et al. ............. 606/61 |
| 5,658,335 A | * | 8/1997 | Allen ........................ 623/17.16 |
| 5,713,898 A | * | 2/1998 | Stucker et al. ................ 606/60 |
| 5,725,582 A | * | 3/1998 | Bevan et al. .................. 606/61 |
| 5,810,816 A | * | 9/1998 | Roussouly et al. ........... 606/61 |
| 5,925,047 A | * | 7/1999 | Errico et al. .................. 606/65 |
| 6,110,173 A | * | 8/2000 | Thomas, Jr. .................. 606/61 |
| 6,136,000 A | * | 10/2000 | Louis et al. ................... 606/61 |
| 6,139,548 A | * | 10/2000 | Errico .......................... 606/61 |
| 6,171,311 B1 | * | 1/2001 | Richelsoph ................... 606/61 |
| 6,217,578 B1 | * | 4/2001 | Crozet et al. ................. 606/61 |
| 6,302,882 B1 | * | 10/2001 | Lin et al. ....................... 606/61 |
| 6,451,019 B1 | * | 9/2002 | Zucherman et al. .......... 606/61 |
| 6,610,093 B1 | * | 8/2003 | Pisharodi ................. 623/17.15 |

* cited by examiner

*Primary Examiner*—Eduardo C. Robert
*Assistant Examiner*—David Comstock
(74) *Attorney, Agent, or Firm*—Bacon & Thomas PLLC

(57) ABSTRACT

A system is designed to fix and recuperate the deformed vertebrae and is formed of a vertebrae-clamping device and an intervertebral fixation block. The vertebrae-clamping device includes two fixation hooks, and a connection portion for use in connecting the two fixation hooks. The intervertebral fixation block comprises a block body, and a joining part for use in joining the block body with the connection portion of the vertebrae-clamping device.

14 Claims, 4 Drawing Sheets

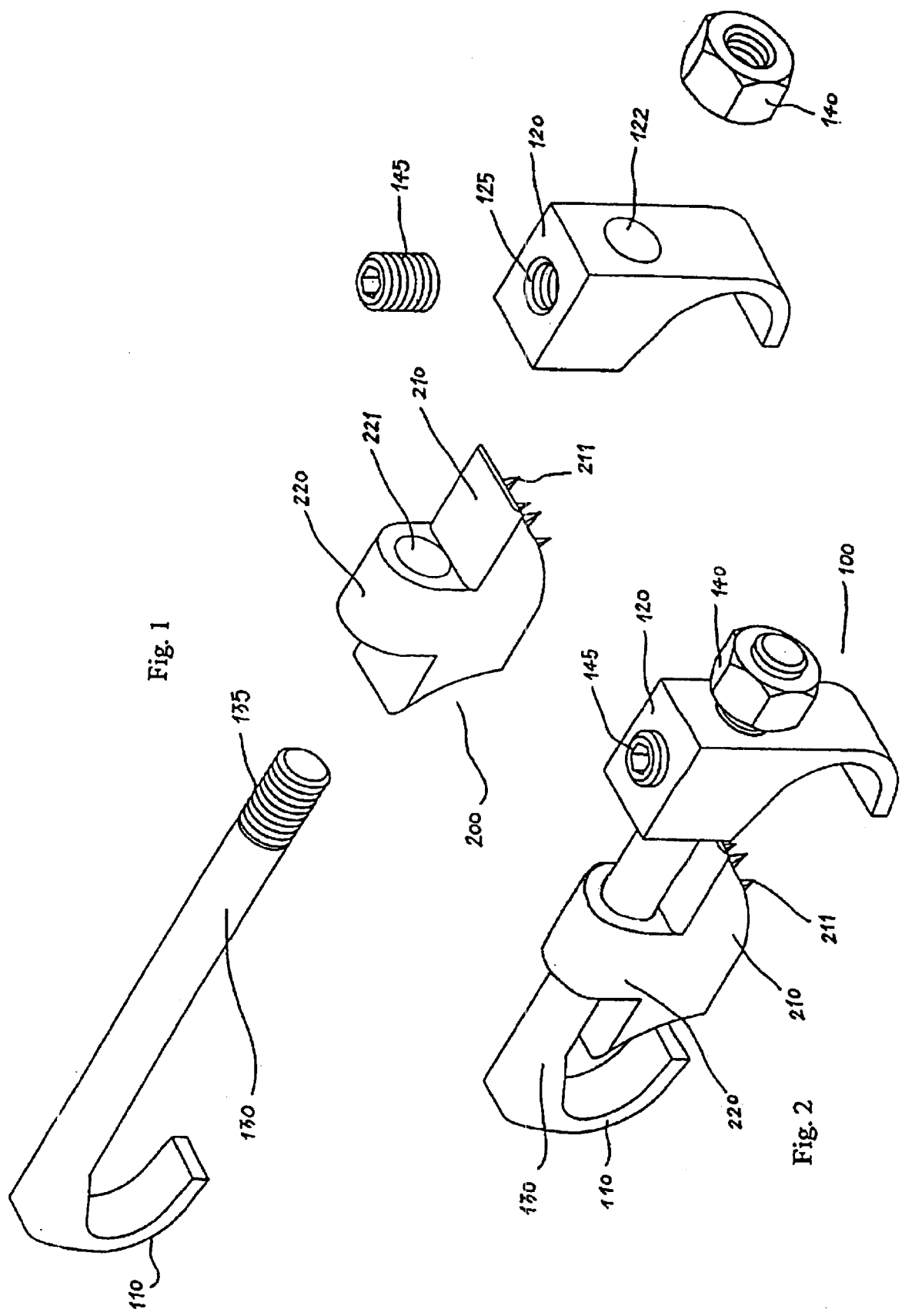

US 6,858,029 B2

SYSTEM FOR FIXING AND RECUPERATING VERTEBRAE UNDER TREATMENT

FIELD OF THE INVENTION

The present invention relates generally to a system for fixing and recuperating the deformed vertebrae, and more particularly to a vertebral fixation and recuperation system having an intervertebral fixation block.

BACKGROUND OF THE INVENTION

U.S. Pat. Nos. 5,454,812 and 5,439,463 disclose a device comprising two fixation hooks and a connection member for clamping and fixing two spinal segments under treatment. These two prior art devices are incapable of fixing effectively the deformed vertebrae, especially the deformed cervical vertebrae.

According to the research done by this inventor of the present invention, the drawback of the prior art devices can be overcome by the addition of an intervertebral fixation block to the prior art devices. In other words, the system of the present invention is suitable for use in fixing and recuperating the deformed spinal segments, such as cervical vertebrae, thoracic vertebrae, and lumbar vertebrae. The present invention is most suitable for use in fixing and recuperating the cervical vertebrae.

SUMMARY OF THE INVENTION

It is the primary objective of the present invention to provide a spinal fixation and recuperation system which is provided with an intervertebral fixation block urging the two vertebrae under treatment.

The spinal fixation and recuperation system of the present invention comprises a vertebrae-clamping device and an intervertebral fixation block. The vertebrae-clamping device includes two fixation hooks, and a connection portion for use in connecting the two fixation hooks. The intervertebral fixation block comprises a block body, and a joining part for use in joining the block body with the connection portion of the vertebrae-clamping device.

The objectives, features, functions and advantages of the system of the present invention will be more readily understood upon a thoughtful deliberation of the following detailed description of the present invention with reference to the accompanying drawings.

BRIEF DESCRIPTION OF THE DRAWINGS

FIG. 1 shows an exploded view of a first preferred embodiment of the present invention.

FIG. 2 shows a perspective view of the first preferred embodiment of the present invention in combination.

DETAILED DESCRIPTION OF THE EMBODIMENTS

Figure 3:
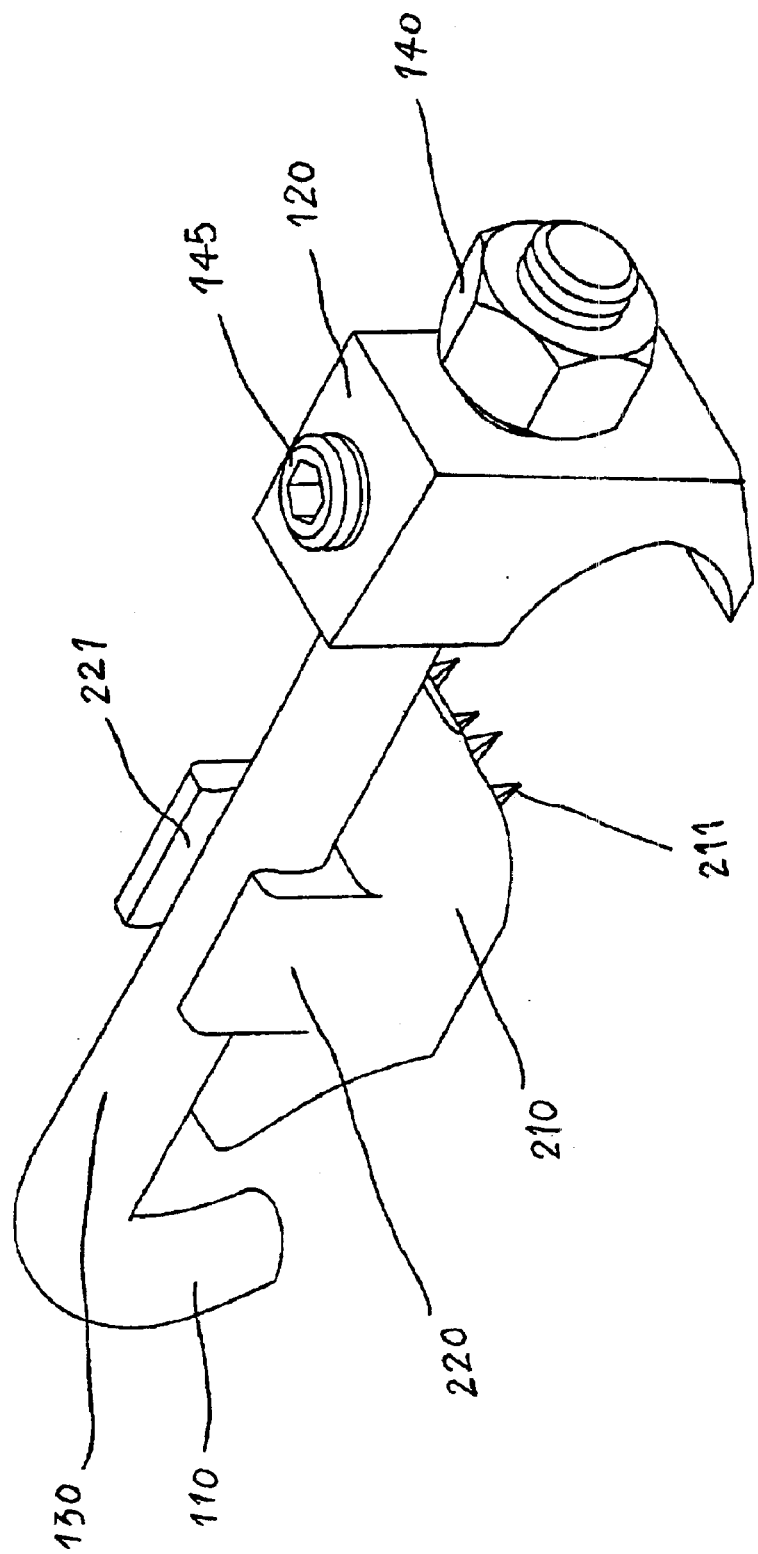
FIG. 3 shows a perspective view of second preferred embodiment of the present invention.

The system of the present invention is designed to fix and recuperate the deformed vertebrae. The system comprises a vertebrae-clamping device and an intervertebral fixation block.

The vertebrae-clamping device comprises two fixation hooks and a connection portion which is used to connect the two fixation hooks.

The intervertebral fixation block comprises a block body, and a joining means for use in joining the block body with the connection portion of the vertebrae-clamping device.

The vertebrae-clamping device of the present invention is basically similar in construction to the prior art devices, such as those which are disclosed in the U.S. Pat. Nos. 5,380,326; 5,439,463; and 5,454,812. Accordingly, the fixation hooks of the vertebrae-clamping device of the system of the present invention are similar in construction to those of the prior art devices. The connection portion of the system of the present invention may be a connection rod or connection cord. The connection portion and the fixation hook of the system of the present invention may be made integrally.

The block body and the joining means of the intervertebral fixation block of the present invention may be made separately or integrally. It is preferable that the block body and the joining means of the present invention are made integrally. The shape and the size of the block body are not limited, depending on the shape and the size of the vertebrae under treatment. Of course, it is desirable to have the block bodies of various shapes and sizes on hand during the surgical operation. The block body has one side which is arcuately projected, and other side which is arcuately recessed. The joining means is preferably opposite to said arcuately-projected side and said arcuately-recessed side. In light of the two sides of the block body being used to fix two vertebrae under treatment, it is preferable that said arcuately-projected side and said arcuately-recessed side of the block body are provided with one or more protrusions for-enhancing the fixation effect of the present invention.

The joining member of the intervertebral fixation block of the present invention may be of any shape and is provided with a fixation hole or slot for use in joining the block body with the connection portion of the vertebrae-clamping device. If the connection portion happens to be a connection cord, the joining member should be provided with the fixation hole, not fixation slot. On the other hand, if the connection portion is a connection rod, the joining member may be provided with the fixation hole, or the fixation slot which is preferable. If necessary, an auxiliary fixation member, such as a screw, may be used in conjunction with a threaded hole of the joining member of the intervertebral fixation block.

As shown in FIG. 1, a vertebrae-clamping device 100 embodied in the present invention comprises two fixation hooks 110 and 120, and a connection portion 130. In addition, the system of the present invention further comprises an intervertebral fixation block 200, which comprises a block body 210 and a joining member 220. The connection portion 130 is put through a fixation hole 221 of the joining member 220 and a through hole 122 of the fixation hook 120 such that outer threads 135 of the connection portion 130 are engaged with a nut 140. The fixation hook 120 is fixed on the connection portion 130 by a screw 145 which is engaged with a threaded hole 125 of the fixation hook 120. The block body 210 is provided in the arcuately-projected side thereof with a plurality of fixation protrusions 211, as shown in FIGS. 1 and 2.

As shown in FIG. 3, the second preferred embodiment of the present invention is basically similar in construction to the first preferred embodiment described above with reference to FIGS. 1 and 2, with the difference being that the joining member 220 of the second preferred embodiment is joined with the connection portion 130 by the fixation slot 221 in conjunction with a lateral screw, if necessary.

Figure 4:
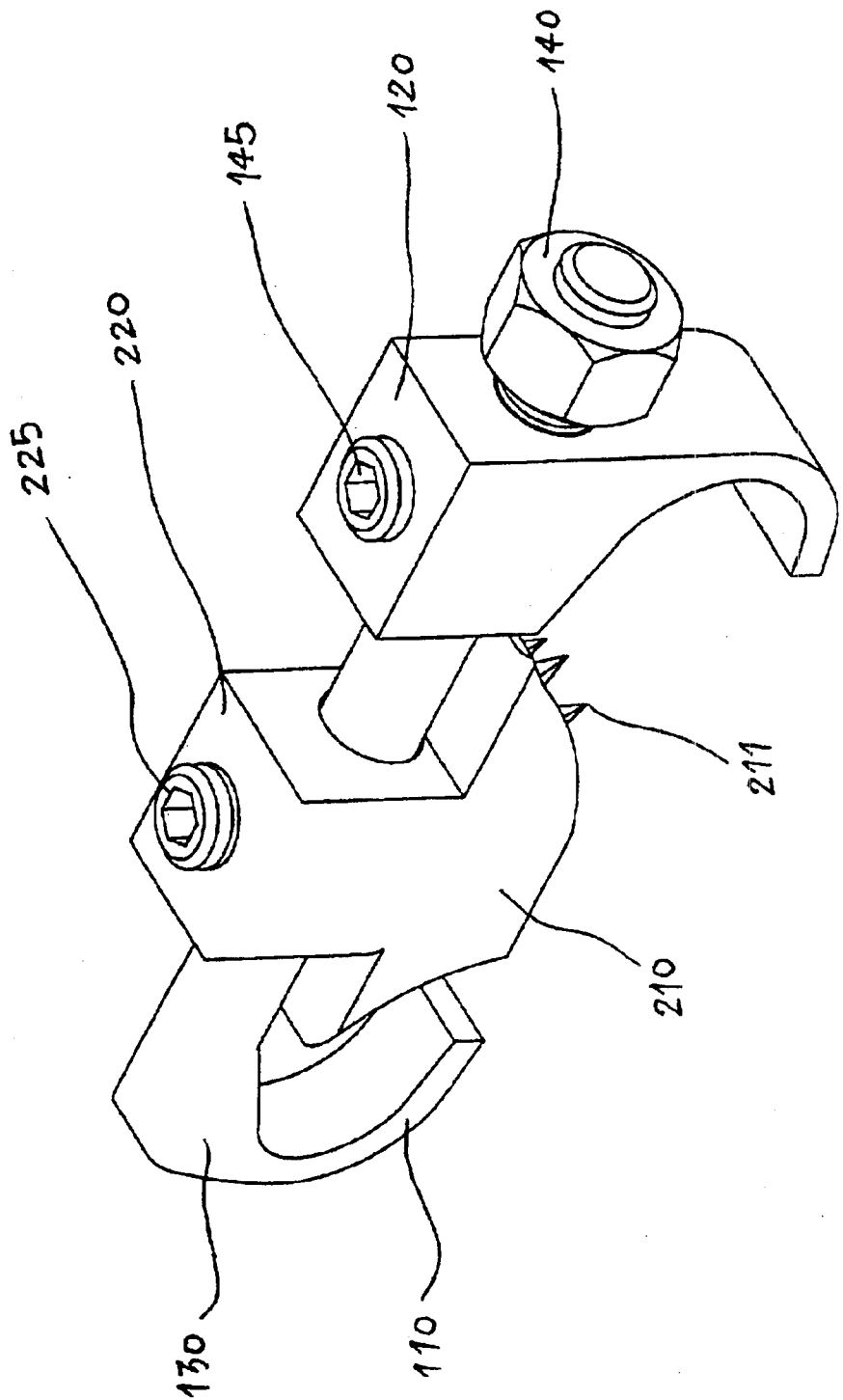
FIG. 4 shows a perspective view of a third preferred embodiment of the present invention.

As shown in FIG. 4, the third preferred embodiment of the present invention is basically similar in construction to the first preferred embodiment described above, except that the former is provided with an auxiliary fixation screw 225 which is engaged with the threaded hole of the joining member 220, so as to fix the joining member 220 at a specific position of the connection portion 130.

Figure 5:
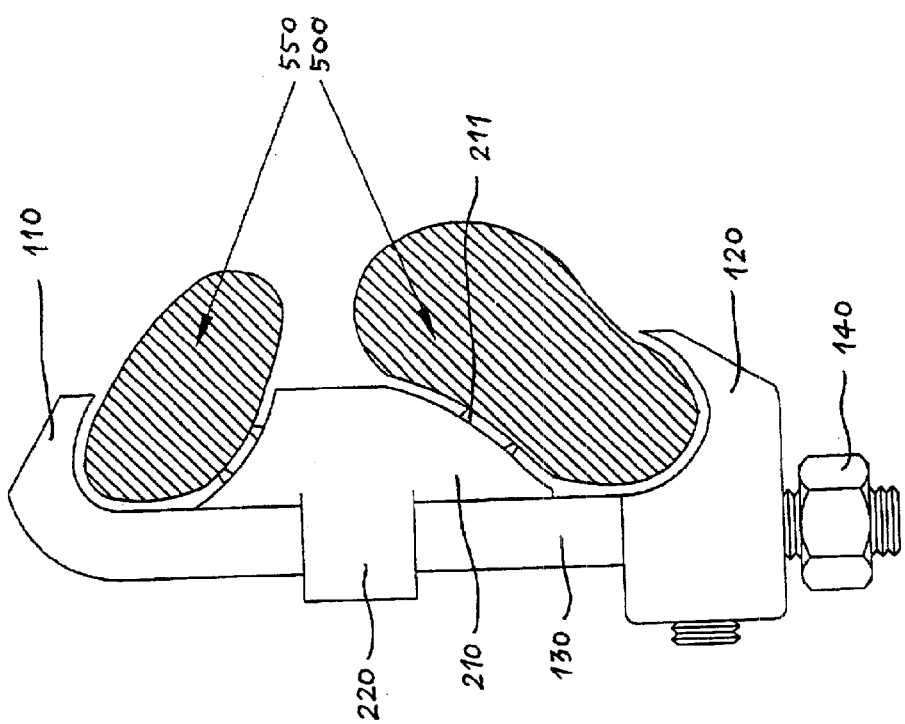
FIG. 5 show a schematic view of the present invention at work.

As illustrated in FIG. 5, the fixation effect of the system of the present invention on two vertebrae 500 and 550 is enhanced by the protrusions 211 of the block body 210 of the intervertebral fixation block 200.

Figure 6:
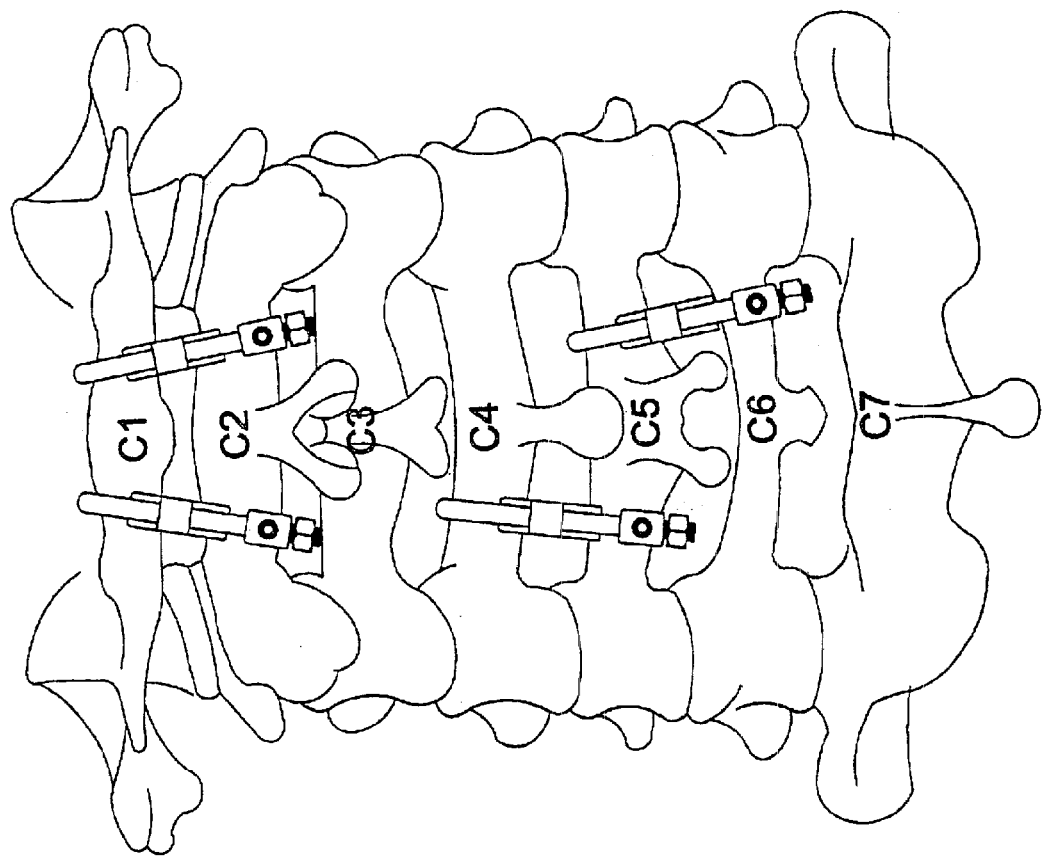
FIG. 6 shows a schematic view of a plurality of system of the present invention at work to fix and recuperate series of cervical vertebrae under treatment.

As illustrated in FIG. 6, a plurality of the systems of the present invention are used to fix and recuperate a series of cervical vertebrae which are designated as C1, C2, C4, C5 and C6. To be more specific, four sets of the systems of the present invention are used to fix and recuperate the cervical vertebrae such that two sets of the systems are used to fix two cervical vertebrae C1 and C2, and that other two sets of the systems are used to fix the cervical vertebrae C4 and C5, as well as C5 and C6.

What is claimed is:

1. A system for fixing and recuperating vertebrae under treatment, said system comprising:
   a vertebrae-clamping device comprising two fixation hooks and a connection portion for connecting said two fixation hooks;
   an intervertebral fixation block comprising a block body, and a joining means for use in joining said block body with said connection portion of said vertebrae-clamping device; and
   wherein said block body is provided with an arcuately-recessed side and an arcuately-projected side, and said block body is used to fix two vertebrae under treatment such that said arcuately-recessed side of said block body urges one of the two vertebrae, and that said arcuately-projected side of said block body urges another one of the two vertebrae.

2. The system as defined in claim 1, wherein said connection portion is a rod body.

3. The system as defined in claim 2, wherein said connection portion is integrally made with one of said two fixation hooks.

4. The system as defined in claim 3, wherein said connection portion is fastened with other one of said two fixation hooks by means of threads.

5. The system as defined in claim 2, wherein said joining means is provided with a fixation hole or fixation slot for use in joining said joining means with said connection portion.

6. The system as defined in claim 1, wherein said block body is provided with a plurality of protrusions for enhancing the fixation effect of said block body on the vertebrae under treatment.

7. The system as defined in claim 1, wherein said arcuately-recessed side and said arcuately-projected side of said block body are provided with a plurality of protrusions.

8. The system as defined in claim 7, wherein said joining means is provided with a fixation hole or fixation slot for use in joining said joining means with said connection portion.

9. The system as defined in claim 1, wherein said joining means is provided with a fixation hole or fixation slot for use in joining said joining means with said connection portion.

10. The system as defined in claim 1, wherein said connection portion is a connection cord; wherein said joining means is provided with a fixation hole for use in joining said joining means with said connection portion.

11. The system as defined in claim 10, wherein said connection portion is fastened with one of said two fixation hooks by means of threads.

12. The system as defined in claim 10, wherein said block body is provided with a plurality of protrusions for enhancing the fixation effect of said block body on the vertebrae to be fixed.

13. The system as defined in claim 1, wherein said joining means is integrally formed with said block body and opposite to said arcuately-recessed side and said arcuately-projected side.

14. A system for fixing and recuperating vertebrae under treatment, said system comprising:
   a vertebrae-clamping device comprising two fixation hooks and a connection portion for connecting said two fixation hooks;
   an intervertebral fixation block comprising a block body, and a joining means for use in joining said block body with said connection portion of said vertebrae-clamping device;
   wherein said connection portion is a connection cord;
   wherein said joining means is provided with a fixation hole for use in joining said joining means with said connection portion; and
   wherein said block body is provided with an arcuately-recessed side and an arcuately-projected side, and said block body is used to fix the two vertebrae under treatment such that said arcuately-recessed side of said block body urges one of the two vertebrae, and that said arcuately-projected side of said block body urges other one of the two vertebrae.

* * * * *